US007214848B2

United States Patent
DiSalvo et al.

(10) Patent No.: US 7,214,848 B2
(45) Date of Patent: May 8, 2007

(54) CATAMENIAL DEVICE CHANGE INDICATOR

(75) Inventors: Anthony DiSalvo, Bernardsville, NJ (US); Raymond J. Hull, Jr., Hampton, NJ (US); William A. James, Hopewell, NJ (US)

(73) Assignee: McNeil-PPC, Inc., Skillman, NJ (US)

(*) Notice: Subject to any disclaimer, the term of this patent is extended or adjusted under 35 U.S.C. 154(b) by 450 days.

(21) Appl. No.: 09/991,407

(22) Filed: Nov. 16, 2001

(65) Prior Publication Data

US 2003/0023214 A1    Jan. 30, 2003

Related U.S. Application Data

(60) Provisional application No. 60/302,060, filed on Jun. 29, 2001.

(51) Int. Cl.
*A61F 13/15* (2006.01)
*A61F 13/20* (2006.01)

(52) U.S. Cl. .................. 604/361; 604/385.17; 604/904

(58) Field of Classification Search ................ 604/361, 604/385.18, 904, 385.17
See application file for complete search history.

(56) References Cited

U.S. PATENT DOCUMENTS

| | | | |
|---|---|---|---|
| 3,706,311 A | 12/1972 | Kokx et al. | |
| 3,794,024 A | 2/1974 | Kokx et al. | |
| 4,172,446 A | 10/1979 | Bucalo | |
| 4,186,730 A | 2/1980 | Bucalo | |
| 4,232,673 A | 11/1980 | Bucalo | |
| 4,816,100 A | 3/1989 | Friese | |
| 5,458,835 A | 10/1995 | Wilkes et al. | |
| 5,674,239 A | 10/1997 | Zadini | |
| 5,813,102 A | 9/1998 | Leutwyler et al. | |
| 6,160,198 A | 12/2000 | Roe et al. | |
| 6,310,269 B1 | 10/2001 | Friese et al. | |

FOREIGN PATENT DOCUMENTS

WO    WO02/00148 A2    1/2002

OTHER PUBLICATIONS

PCT International Search Report, dated Sep. 20, 2002, for PCT Int'l. Appln. No. PCT/US02/17140.

*Primary Examiner*—Michele Kidwell

(57) ABSTRACT

An absorbent device for insertion into a vaginal cavity, the absorbent device having an absorbent body and an indicator structure arranged and configured within the absorbent body, the indicator structure having a resilient member maintained in a strained configuration by a restraint; wherein the resilient member is capable of reverting to a relaxed configuration upon the weakening of the restraint and the restraint weakens upon exposure to moisture.

2 Claims, 8 Drawing Sheets

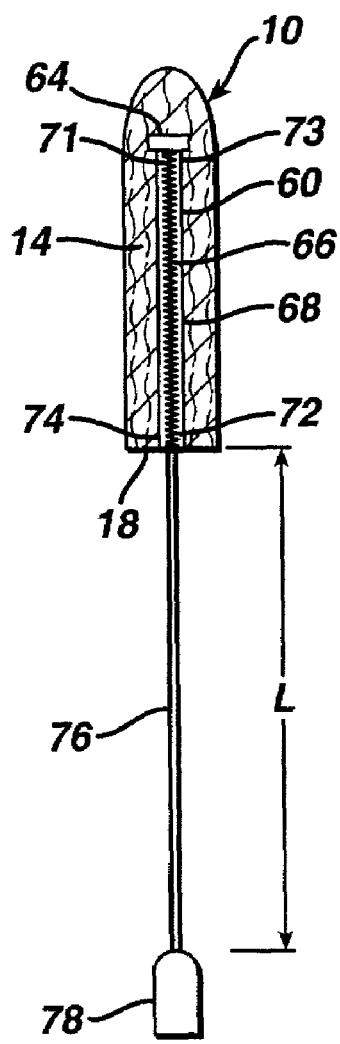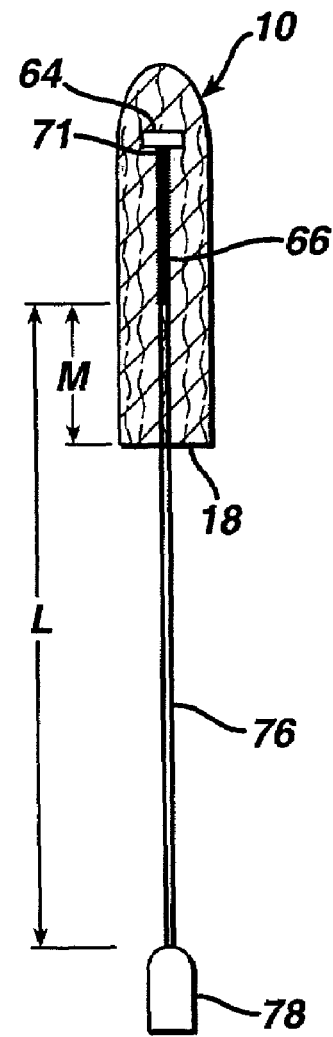

CATAMENIAL DEVICE CHANGE INDICATOR

CROSS-REFERENCE TO RELATED APPLICATION

This application claims the benefit of provisional application Ser. No. 60/302,060 filed on Jun. 29, 2001.

FIELD OF THE INVENTION

The present invention relates to tampons, and more particularly to a tampon wetness detection system that signals the user that the tampon is approaching absorbent capacity and it is time to change the tampon.

BACKGROUND OF THE INVENTION

Tampons are designed to contain a particular amount of menstrual fluid. The amount of menstrual fluid absorbed by a tampon can vary depending on absorbency levels. For example, in the United States, tampon absorbency can range from less than 6 grams (Junior absorbency) grams to 15–18 grams (Ultra absorbency). In order to ascertain whether a tampon has reached its absorbent capacity, the tampon must be removed and viewed, resulting in the destruction of the tampon, as most women are reluctant to reinsert the tampon. In most cases, a user will remove a tampon before it has reached its absorbent capacity in order to prevent an accident wherein the absorbent capacity of the tampon is exceeded. Once the absorbent capacity is exceeded, the excess menses flows unimpeded from the vagina to soil the user's clothing.

A determinative criteria frequently used to gauge tampon replacement is the amount of time elapsed since insertion. The time elapsed criteria for changing tampons is not satisfactory for several reasons, e.g., the menstrual flow rate varies throughout the menstruating period and much adsorbent capacity of tampons is wasted due to the tendency to change before an accident occurs.

The flow variation throughout the period causes problems as to how long to wear a tampon because a user cannot establish a definite time period for which the absorbent capacity within a tampon is sufficient. Therefore, she is in a quandary as to how long to wear specific tampons during days of heavy flow as contrasted to days of light flow.

A correlation between tampon performance during light flow versus heavy flow is difficult for the user to make. Thus, since the user would rather be safe than sorry, she frequently removes a tampon before the absorbent capacity of the tampon has been reached and wastes much of the product she had purchased.

Tampons have been made larger and with different materials to obtain higher absorbencies, often resulting in product claims that a user would not have to change the tampon as often. But the user would still waste a portion of the tampon absorbent capacity, as most users are not willing to risk having an accident. Therefore, bigger tampons provide a longer wearing time but do not approach the problem of fully using the absorbent capacity within a tampon. In rare cases, should a user leave the tampon in for an extended period of time, a life threatening infection may develop.

Wearing a high absorbency tampon can lead to discomfort and other problems as well. Women will sometimes wear a larger absorbency tampon due to the fear of tampon failure, especially if she is uncertain how often she will be able to access privacy in order to change the tampon. If the tampon is unsaturated, there may be drying of the vaginal wall, which may cause discomfort upon the tampon's removal.

Thus, there is a need for a tampon wetness detection system that signals the user to change the tampon prior to soiling the user's clothing.

SUMMARY OF THE INVENTION

An absorbent device for insertion into a vaginal cavity, the absorbent device having an absorbent body and an indicator structure arranged and configured within the absorbent body, the indicator structure having a resilient member maintained in a strained configuration by a restraint; wherein the resilient member is capable of reverting to a relaxed configuration upon the weakening of the restraint and the restraint weakens upon exposure to moisture.

BRIEF DESCRIPTION OF THE DRAWING

FIG. 9 is a cross-section of another embodiment of the invention.

FIG. 10 is a cross-section of the embodiment of FIG. 9 showing the resilient member in a relaxed configuration.

DETAILED DESCRIPTION OF THE PREFERRED EMBODIMENTS

Figure 1:
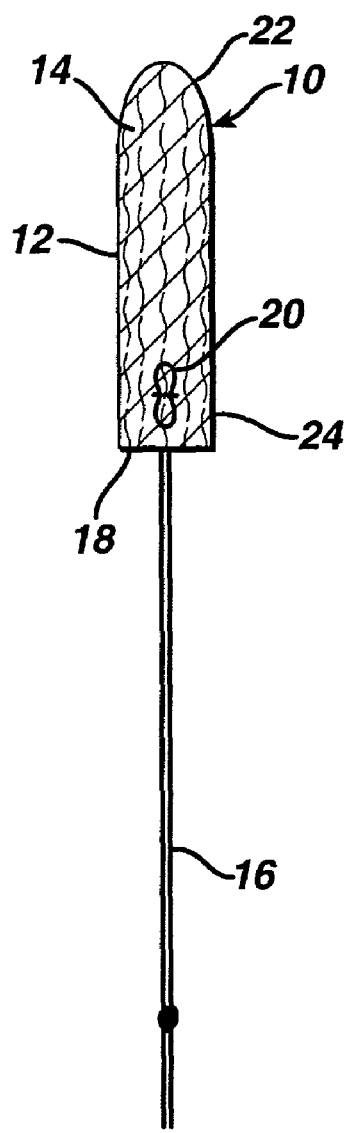
FIG. 1 is a cross-section of a tampon showing a resilient member held in a strained configuration by a restraint according to one embodiment of the invention.

Resilience herein means the capability of a strained body to recover its size and shape after deformation caused especially by bending, compressing, twisting, stretching or any combination thereof. A resilient member can go from a relaxed configuration to a strained configuration to a relaxed configuration any number of times without losing substantially the ability to recover its original shape. A resilient member in a strained configuration possesses strain energy or potential energy of deformation. In the present invention, the release of the stored potential energy may cause the resilient member to revert to the relaxed configuration, resulting in a potential for kinetic movement—movement of portions of the resilient member within the catamenial device. By this movement or motion, the user may feel an appreciable vaginal tactile sensation.

As used herein the specification and the claims, the term "weaken" and variants thereof describe the loss of strength and/or integrity of a material, especially upon exposure to fluid or moisture. The material may loose its cohesive or adhesive nature, swell, dissolve or simply weaken such that it no longer can perform as in a dry state. Thus, the material no longer has the strength to restrain the resilient member in a strained configuration.

In general, the absorbent article of this invention has at least two parts: a catamenial absorbent device and a wetness indicating structure. The wetness indicating structure may be a single unit or may have multiple components. The catamenial device may be a tampon and can also be either a tampon used with an applicator or one that is inserted digitally.

In the present invention, as seen generally in the Figures, tampon 10 has an absorbent core 14, resilient member 20, an upper portion 22, a lower portion 24, lower edge 18 and may optionally include string 16 and cover 12 covering absorbent core 14. Resilient member 20 may be a ring, sheath, spring or any other shaped device that may go from a natural, relaxed configuration into a strained configuration and back to the relaxed configuration. The strained configuration of resilient member 20 is maintained by restraint 21. In the present embodiment, resilient member 20 is held and maintained in a strained configuration by restraint 21 while the tampon is in a dry state. Upon penetration of fluid into the tampon, restraint 21 weakens, which allows resilient member 20 to assume its original, more relaxed configuration. Preferably, this relaxation occurs as a quick release, leading to a tactile sensation.

Figure 2:
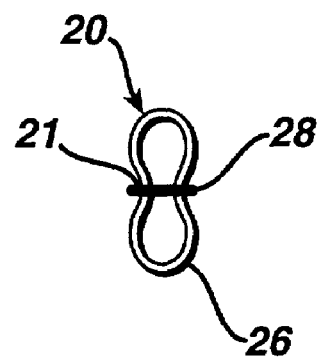
FIG. 2 is a cross-section showing the resilient member of FIG. 1 in further detail.
Figure 3:
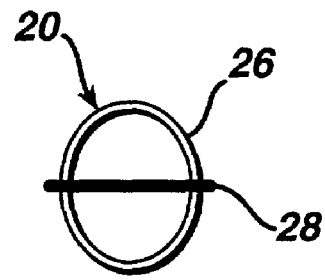
FIG. 3 is a cross-section showing the resilient member of FIG. 1 in a relaxed configuration.

As seen in FIGS. 1–3, resilient member 20 is shown as ring 26. When in a relaxed state, ring 26 is circular as shown in FIG. 3. In a strained state, ring 26 may be restrained by tie 28 (shown FIG. 2). Tie 28 may be in the shape of a string, ring or band and may be formed of a material that is capable of weakening upon exposure to an aqueous fluid, e.g., menstrual fluid. The shape of the tie is not important as long as tie 28 is capable of restraining ring 26 in a strained configuration. Upon exposure to fluid, tie 28 looses integrity and weakens or softens such that the stored potential energy of restrained ring 26 overcomes the restraint forces of tie 28 and thereby assumes its natural, circular shape. Tie 28 may be stretched or ruptured by the kinetic energy of motion when ring 26 relaxes. The relaxation forces of spring 26 must be sufficiently great enough to rupture or stretch tie 28 after tie 28 is exposed to fluid.

The tie or restraint can be made from any soluble, water swellable material or any material that weakens or looses integrity upon exposure to fluid or moisture. These materials include but are not limited to gelatins, water soluble adhesives, cellulose derivatives including HPMC (hydroxypropyl methyl cellulose) and ethyl cellulose, polyvinyl alcohol, polyether urethane, polyethylene oxide, polyacrylamide and copolymers thereof, and polyacrylic acid. Materials that loose the ability to form cohesive bonds upon exposure to fluid may also be used. The restraint may be in the form of a ribbon, a band or a drop that sets and forms a bond, as in the case of an adhesive.

Additionally, tie 28 or resilient member 20 may have other shapes or embodiments. For example, resilient member 20 may be an "open ring" having first and second ends with a space between the ends. The open ring end may be compressed such that the first end overlaps and is adhered to the second end by a soluble adhesive. Upon contact with menstrual fluid, the adhesive would loose integrity or adhesive properties, releasing the first end to give a tactile sensation. Another embodiment may be a coil spring (similar to that found in a ballpoint pen) that is compressed and held by a soluble polymer or adhesive. The coil-type spring may be placed within tampon 10 such that the spring points outward towards cover 12 and is parallel to edge 18. Once the polymer or adhesive looses integrity by softening or weakening, the spring can return to its original, uncompressed shape. The polymer may loose the ability to be cohesive while the adhesive may loose the ability to adhere. Still another embodiment may be an inflated sphere that is compressed about the central diameter.

As previously mentioned, the resilient member may be made from any resilient material capable of undergoing a deformation without loosing the ability to recover its original shape. A non-limiting list of these materials include elastomers and plastics such as polyacetals, polyolefins (e.g., polyethylenes and polypropylenes), nylons, rubbers, polyurethanes; and metals such as copper, stainless steel, spring steel, titanium, nickel, nitinol, and metals coated with any type of non-corrosive coating such as elastomers or plastics.

Resilient member 20 may be placed anywhere in the tampon but it is preferable that it be located near to lower portion 24 of tampon 10. While not being bound by any particular theory, it is believed that the vagina has a sensitive region surrounding the introitus and would be more receptive to the tactile movement of the wetness indicator.

Upon use, tampon 10 is inserted into the vagina. As menstrual fluid flows from the cervix into the vagina, the fluid permeates the absorbent material of tampon 10. Once the fluid has reached the inner portion of the absorbent material, tie 28 begins to weaken and dissolve (weakened tie 28' shown in FIG. 3). When the stored potential energy of ring 26 overcomes the restraining forces of tie 28, tie 28 will be unable to restrain ring 26 in bent or stretched form. Ring 26 will return to its original circular form, releasing kinetic energy and giving a tactile or noticeable response to the wearer.

Figure 4:
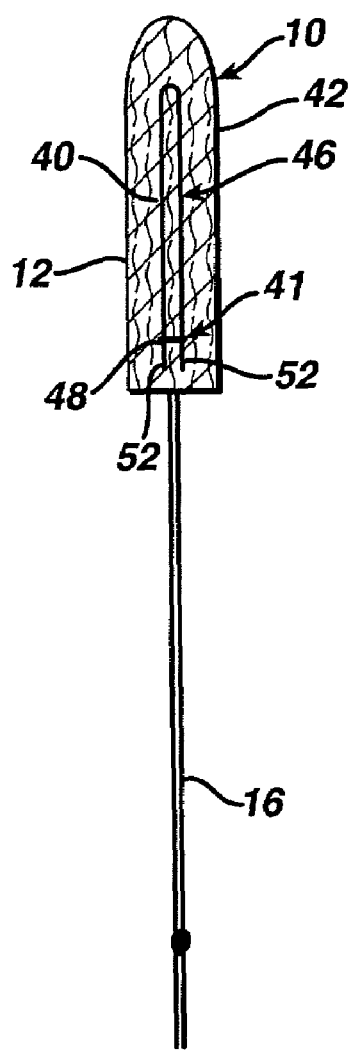
FIG. 4 is a cross-section of a tampon showing a compressed resilient member held in a strained configuration by a restraint according to another embodiment of the invention.
Figure 5:
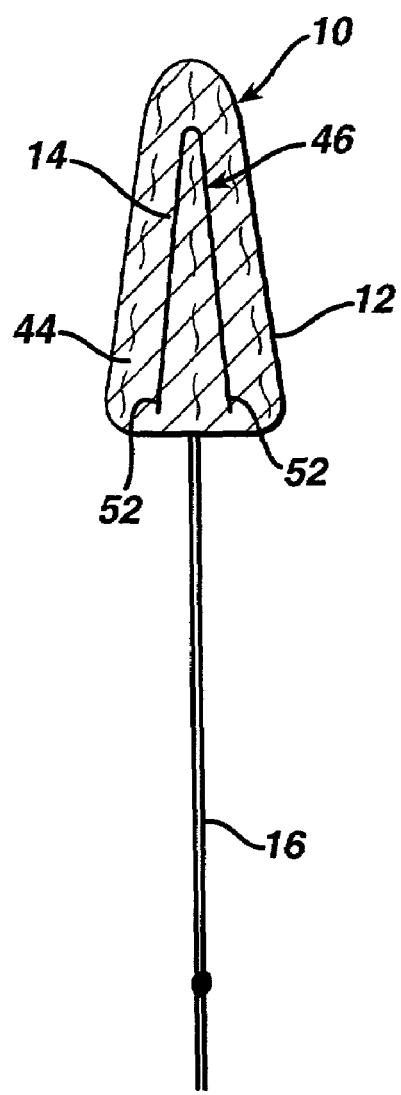
FIGS. 5, 5a, 5b are cross-sections of a tampon showing the resilient member of FIG. 4 in a relaxed configuration.

Turning to FIGS. 4–5, another embodiment is shown. FIG. 4 shows resilient member 40 contained with in tampon 10. Resilient member 40 has compressed spring 44, held by restraint 41. An example of a restraint is tie 48. Upon exposure to fluid, tie 48 weakens, releasing spring 46 to an unbent state thereby giving the wearer a tactile sensation. Spring 46 in an unbent state is shown in FIG. 5. As previously mentioned, in order for the tactile sensation to be recognized it is believed that the resilient member should open in the lower portion of tampon 10. In the case of the embodiment shown in FIGS. 4–5, the resilient member must be made from materials that are resilient enough to give a noticeable sensation but yet weak enough so as not to push through the absorbent material of tampon 10, and thereby potentially damage the vaginal walls, especially when tampon 10 is removed. Guards may be placed over ends 52 of resilient member 14 or cover 12 may be made of such material to completely contain ends 52 so that ends 52 do not puncture the absorbent materials. As resilient member 40 reaches an unrestrained state, ends 52 may distort or push out the absorbent material 14 and cover 12 of lower portion 44. A representation is shown in FIG. 5.

Figure 5A:
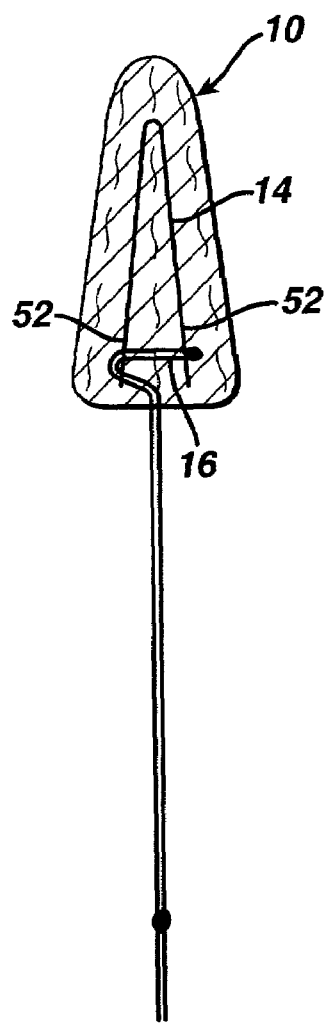
Figure 5B:
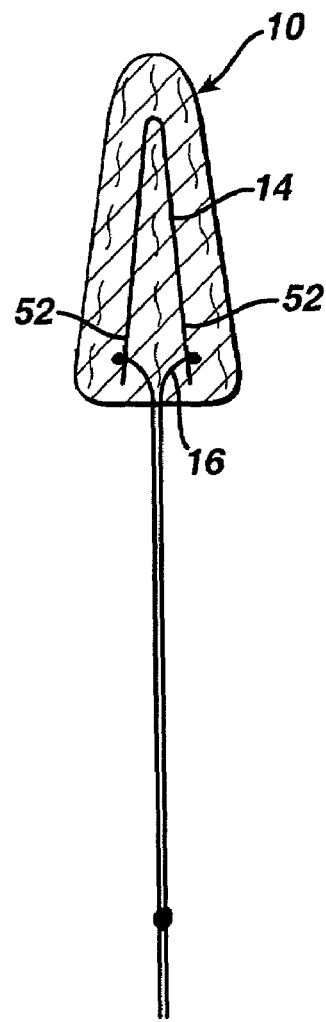

Additionally, removal string 16 may thread through or be attached to ends 52 of resilient member 14 such that when string 16 is pulled for withdrawal, ends 52 are drawn together (seen in FIGS. 5*a* and 5*b*).

Figure 5C:
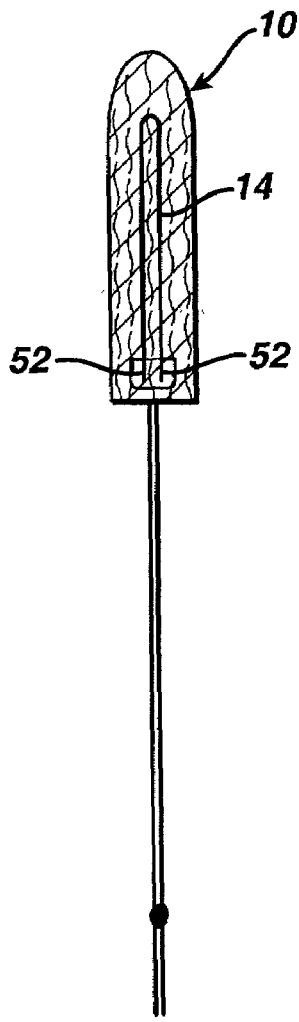
FIG. 5c is a cross-section of a tampon showing the ends of resilient member of FIG. 4 restrained by an alternate restraint.

Alternately, in this embodiment, tie 48 may be replaced by a restraint such as a soluble gelatin cap, the gelatin similar to what is used to encapsulate various pharmaceutical and over-the-counter drugs. The cap could slide over ends 52 of resilient member 14 thereby restraining the ends (seen in FIG. 5*c*).

Resilient member 40 may be smaller than represented in FIGS. 4 and 5 and may alternately be inverted such that ends 52 are toward upper portion 42 of tampon 10. Additionally, in another embodiment, resilient member 40 may have multiple prongs. The restraint may be in the form of an adhesive or other chemical bond. Any polymer or adhesive that weakens in fluid can form this type of restraint.

Figure 6:
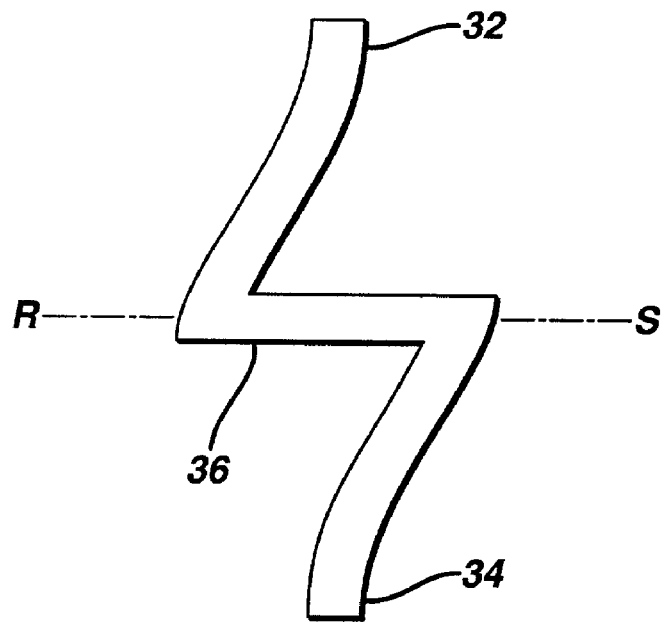
FIG. 6 is a front elevation of a resilient member in a relaxed state according to an alternate embodiment of the invention.
Figure 7:
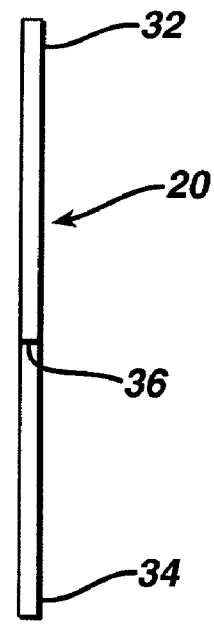
FIG. 7 is a side elevation of the resilient member of FIG. 6.
Figure 8:
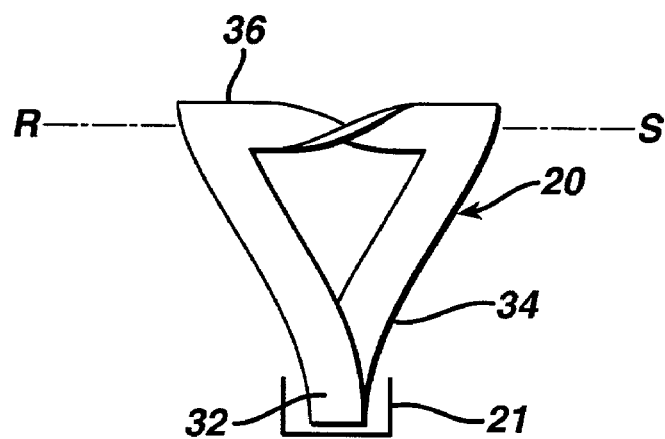
FIG. 8 is a front elevation showing the ends of the resilient member of FIG. 6 restrained.

FIGS. 6–8 show an alternate embodiment of resilient member 20. Resilient member 20 has a first portion 32, second portion 34, which are connected by central portion 36. The side elevation, FIG. 7, shows that the resilient member in relaxed configuration is planar. By bending first portion 32 toward second portion 34, the central portion 36 is twisted about central axis "RS". The first portion 32 and second portion 34 are held in close proximity by restraint 21. In a preferred embodiment (and what is shown in FIG. 8), restraint is a cap similar to that described above, although any type of restraint may be used.

FIGS. 6 and 7 shown an alternate embodiment in which the tactile sensation is not from the pressure of a resilient member going from a bent or strained state to a relaxed state but from movement of the withdrawal string.

FIG. 6 shows tampon 10 having wetness indicator 60 contained within absorbent core 14 and string 76 having a length L. Spring 66 is contained within and held in an expanded form by sheath 68. Upper end 71 of spring 66 and upper end 73 of sheath 68 are connected to upper anchor 64. Lower end 72 of spring 66 is connected to lower edge 18 of tampon 10. Lower end 74 of sheath 68 is connected to lower end 72 of spring 66. String 76 is also connected to upper anchor 64. Upon insertion and use, penetration of fluid causes the weakening or dissolution of sheath 68. Although sheath 68 may also break away from lower edge 18 of tampon 10 it is not necessary for spring 66 to constrict into its natural form as long as sheath 68 has weakened sufficiently for the forces of spring 66 to overcome the holding restraining forces of sheath 68. When the restraining forces of sheath 68 are overcome, spring 66 constricts to its natural form with upper end 71 connected to upper anchor 64. This constriction toward upper anchor 64 pulls string 76 through the vaginal opening and upward into tampon 10 for a distance of M. The amount of movement, M, is dependent on the resiliency of spring 66. The length of string 76 remaining outside the body is L–M.

Additionally, string-grasping member 78 can be attached to the end of string 76. String grasping member 78 aids in removal of tampon 10 and also aids in detection of string movement.

Spring 66 may be any resilient device that is capable of being stretched from an initial relaxed configuration to a temporary elongated configuration. Examples may be elastic bands or rings distorted from a circular shape to an elongated, oval shape. In the case of the last example, the ring would return to circular shape when the sheath dissolves.

Another embodiment is shown in FIGS. 8–9. Tampon 10 contains resilient member 120, lower portion 132, upper anchor 124, lower edge anchor 134, and string 136. Resilient member 120 has spring 126 contained within sheath 128. Spring 126 is attached to upper anchor 124 and lower anchor 134. In a dry state, spring 126 is stretched to length X, enclosed within sheath 128 and connected to upper anchor 124 and lower anchor 134. Upon exposure to fluid, sheath 128 dissolves, which allows spring 126 to constrict to length Y, Y being the natural, unstressed state of spring 126. The decrease from length X to length Y causes lower portion 132 of tampon 10 to bulge out, thereby causing a tactile sensation to the wearer.

Another embodiment is shown in FIGS. 10–14. This embodiment combines two wetness indicators to give dual tactile indications that the tampon is nearing saturation. As seen in FIG. 10, wetness indicator 80 has a resilient member 82 and string 96. String 96 is affixed to resilient member 82 at attachment 84 and is slideably attached to resilient member 82 at slide 85. String 96 may be attached to resilient member 82 at attachment 84 by any known methods including tying, permanent gluing, heating, etc. Additionally, string 96 may be slideably attached to resilient member 82 at slide 85 by any known means such as threading through resilient member 82 or being guided through a sheath, etc. String 96 may also be slideably attached on the side of resilient member 82. In the embodiment shown in FIG. 10, resilient member 82 is a ring 86 having middle portion 91, upper portion 92 and lower portion 93.

Figure 11:
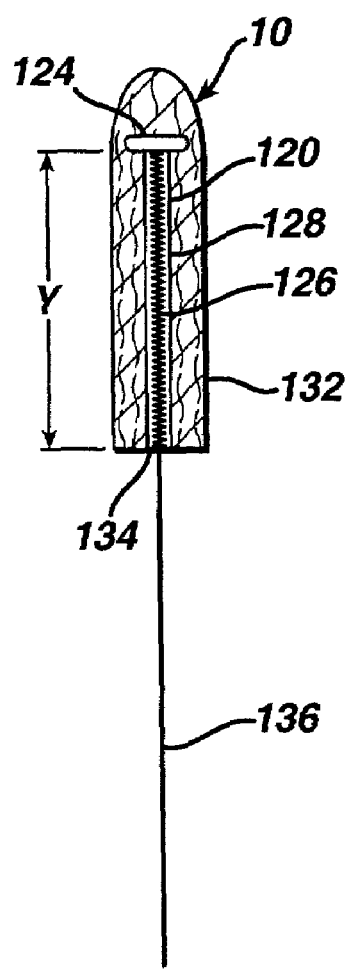
FIG. 11 is a cross-section of a tampon showing a strained resilient member according to another embodiment of the invention.
Figure 12:
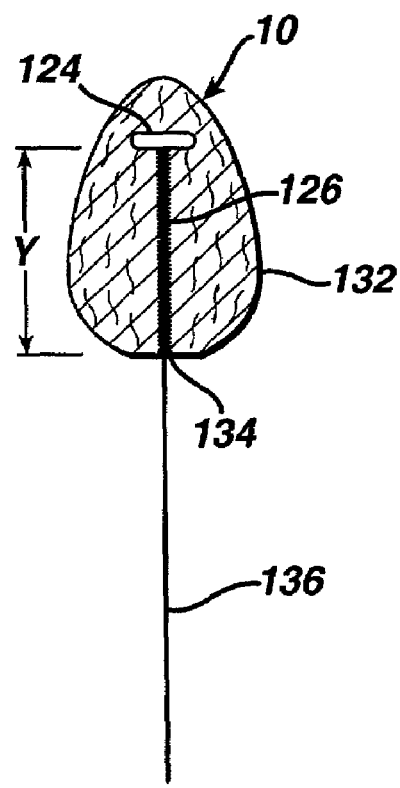
FIG. 12 is a cross-section of the embodiment of FIG. 11 showing the resilient member in a relaxed configuration.
Figure 13:
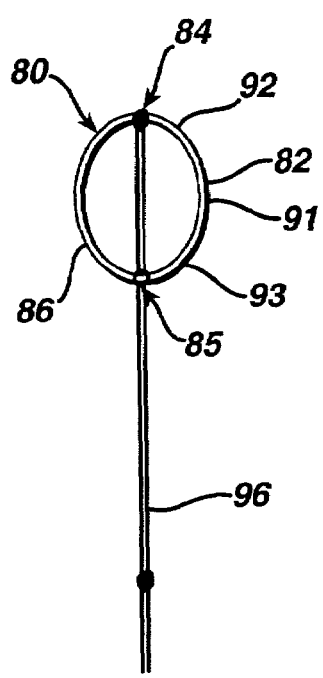
FIG. 13 is a plan view of a resilient member of another embodiment.
Figure 14:
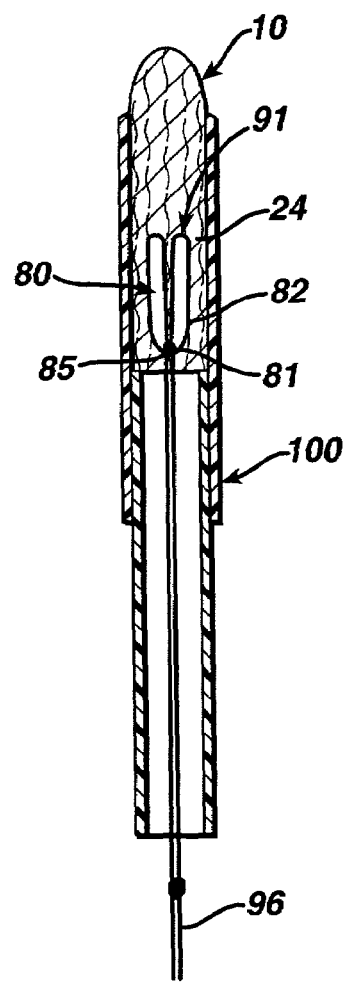
FIG. 14 is a cross-section of an applicator containing a tampon having the resilient member of FIG. 13.
Figure 15:
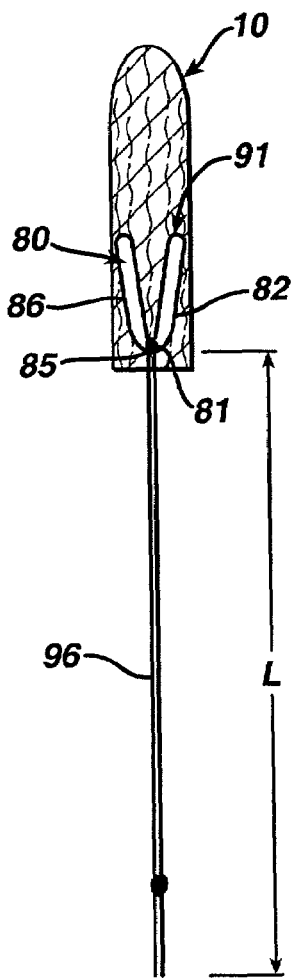
FIG. 15 is a cross-section of a tampon containing the resilient member of FIG. 13 after insertion.
Figure 16:
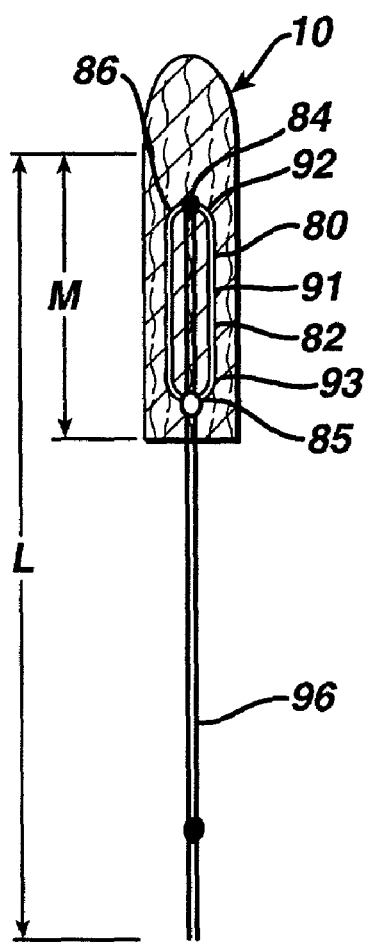
FIG. 16 is a cross-section of a tampon containing the resilient member of FIG. 13 after the anchoring point has softened and the ring has actuated.
Figure 17:
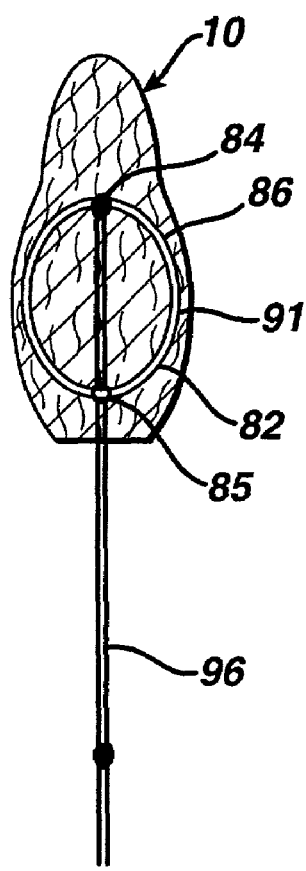
FIG. 17 is a cross-section of a tampon containing the resilient member of FIG. 13 in a relaxed configuration.

FIG. 11 shows tampon 10 contained within applicator 100. When compressed and placed into tampon 10, upper portion 92 and lower portion 93 of ring 86 are brought closer together and constrained at slide 85 by restraint 81. Restraint 81 may be a in the form of a tie made from materials capable of weakening, a bonding polymer or adhesive or any means of securing the resilient member 82 such that it is in a strained configuration. Upper portion 92 and lower portion 93 can be but do not necessarily have to be touching or in close contact. The joined upper portion 92 and lower portion 93 are positioned in lower tampon portion 24. In FIG. 12, as seen similarly in FIGS. 6 and 7, string 96 has initial length L. Middle portion 91 of ring 86 is toward the upper tampon portion. Upon insertion into the vaginal cavity (seen in FIG. 12), tampon 10 begins to absorb fluid. After fluid has penetrated the absorbent material 14, restraint 81 begins to weaken. When restraint 81 is sufficiently weakened, upper portion 92 and lower portion 93 are released and allowed to return to a relax configuration. This is seen in FIG. 13. String 96 has fed through slide 85, resulting in a decrease of M in length L outside the body and a tactile sensation to the wearer. The decrease in string length is proportional to the diameter of ring 86. Additionally, as seen in FIG. 14, middle portion 91 of ring 86 simultaneously expands, resulting in another tactile sensation to the vaginal walls.

Alternately, string 96 may be permanently affixed to lower portion 93 of ring 86 at slide 85 and threadable through upper portion 92 at attachment 84. When ring 86 expands, string 96 is pulled up and when resilient member 82 (shown as ring 86) is in a fully relaxed configuration, string 96 may be shortened as much as two times the length of the diameter of ring 86.

Detection by the wearer of the wetness indicator is preferably subtle enough not to startle the user and elicit an appreciable response. It is preferred that the resilient member have a quick release or expansion from the strained state to the relaxed state in a fashion to be noticeable. A slow expansion may be less discernible to the wearer.

Absorbent tampons are usually substantially cylindrical masses of compressed absorbent material having a central axis and a radius that defines the outer circumferential surface of the tampon. Tampons are often formed by first obtaining a shaped mass of absorbent material called a tampon blank. This blank can be in the form of a roll of sheet-like material, a segment of a continuous absorbent material, a mass of randomly or substantially uniformly oriented absorbent material, an individually prepared or cast mass of absorbent material, and the like.

The tampon blank is relatively uncompressed and has a relatively low density. It may be compressed to form a product having overall dimensions less than those of the blank prior to use. The compressed tampons may have a generally uniform density throughout the tampon, or they may have regions of differing density as described in the commonly assigned applications to Friese et al., U.S. Ser. No. 07/596,454, and Leutwyler et al., U.S. Pat. No. 5,813,102, the disclosures of which are herein incorporated by reference. Tampons also usually include a cover or some other surface treatment and a withdrawal string or other removal mechanism.

It is preferred that the wetness indicator of the present invention be contained within the central portion of the tampon.

Another type of tampon that may contain a wetness indicating device may be the bag or sack-type tampon. In this type of tampon, absorbent material is contained within a overwrap that is at least partially fluid permeable. Examples of bag-type tampons are disclosed in U.S. Ser. No. 09/741,718 (Buzot), U.S. Ser. No. 09/823,045 (Buzot) and U.S. Ser. No. 09/874,451 (Intravartolo et al.), the entire contents which are hereby incorporated by reference.

Absorbent material useful in tampon formation includes fiber, foam, superabsorbents, hydrogels, and the like. Preferred absorbent material for the present invention includes fiber and foam.

Preferably, the fibers include hydrophilic fibers, and more preferably, the fibers include absorbent fibers, i.e., the individual fibers, themselves, absorb fluid. A useful, non-limiting list of useful tampon fibers includes natural fibers such as cotton, wood pulp, jute, and the like; and processed fibers such as regenerated cellulose, cellulose nitrate, cellulose acetate, rayon, polyester, polyvinyl alcohol, polyolefin, polyamine, polyamide, polyacrylonitrile, and the like. Other fibers in addition to the above fibers may be included to add desirable characteristics to the absorbent body. For example, hydrophobic fibers may be used in outer surfaces of the tampon to reduce surface wetness and hydrophilic fibers may be used to increase the rate of fluid transport into and throughout the body. Preferably, the tampon fibers are rayon or cotton, and more preferably, the fibers are rayon. The fibers may have any useful cross-section.

Preferred fiber cross-sections include multi-limbed and non-limbed. More preferably, the fibers are predominantly multi-limbed. Multi-limbed, regenerated cellulosic fibers have been commercially available for a number of years. These fibers are known to possess increased specific absorbency over non-limbed fibers. One commercial example of these fibers are the Danufil VY multilimbed viscose rayon fibers available from Acordis Ltd., London, England. These fibers are described in detail in Wilkes et al., U.S. Pat. No. 5,458,835, the disclosure of which is hereby incorporated by reference.

Preferably, the foams include hydrophilic foams, and more preferably, the foams may include absorbent foams, i.e., the foam cells, themselves, absorb fluid.

A fluid-permeable cover may substantially enclose the tampon blank. Thus, the cover encloses a majority of the outer surface of the tampon. This may be achieved as disclosed in Friese, U.S. Pat. No. 4,816,100, the disclosure of which is herein incorporated by reference. In addition, the cover may enclose either or both ends of the tampon. Of course, for processing or other reasons, some portions of the surface of the tampon may be free of the cover. For example, the insertion end of the tampon and a portion of the cylindrical surface adjacent this end may be exposed, without the cover to allow the tampon to more readily accept fluids.

The cover can ease the insertion of the tampon into the body cavity and can reduce the possibility of fibers being separated from the tampon. Useful covers are known to those of ordinary skill in the art. They may be selected from an outer layer of fibers which are fused together (such as by thermobonding), a nonwoven fabric, an apertured film, or the like. Preferably, the cover has a hydrophobic finish.

The wetness indicating device can be inserted into the tampon blank prior to compression when the winding mandrel first rolls the nonwoven ribbon into an essentially cylindrical form. The wetness indicating device can also be inserted into the voids left when the winding mandrel is removed from the cylindrical form. Alternately, the wetness indicating device can be inserted after compression.

If other materials such as foam are used to make the tampon, the resilient member may be inserted through a slit cut into the lower portion of the tampon. Additionally, if the tampon has a cover, the resilient member can be placed between the cover and absorbent material, encircling the absorbent material. This may indent the tampon.

Tampons are generally categorized in two classes: applicator tampons and digital tampons. Applicator tampons use a relatively rigid device to contain and protect the tampon prior to use. To insert the tampon into a body cavity, the applicator is partially inserted into the body cavity, and the tampon can be expelled therefrom. Because the rigid applicator device protects the tampon, the tampon need not have a high degree of dimensional stability. In contrast, digital tampons do not have an applicator to help guide them into the body cavity and require sufficient stability to allow insertion without using an applicator.

EXAMPLE

Sheets of polyacetal having known thicknesses were cut into strips approximately ¼ inch wide. Using a flameless electric heat gun, each strip was heated in the central portion until the central portion was sufficiently pliable to be bent to form a known angle. Two arms connect the central portion. The arms of the strip were then trimmed to a length approximately 45 mm long.

A dissolvable capsule used in a common over-the-counter medication was opened and the contents discarded. The capsule yielded two portions, a larger cap and a smaller cap.

The larger cap was slid over the two arms of the bent strip, restraining the bent strip in a shape similar to a hairpin.

Each restrained strip was placed into water of a known temperature. The time required for the cap to weaken sufficiently for the strip to go to the relaxed configuration was measured.

TABLE 1

| Sample | Thickness of strip (inches) | Width of strip (inches) | Angle of central portion | Water temperature (degrees F.) | Time to dissolve (seconds) |
|---|---|---|---|---|---|
| 1 | 0.065 | 0.25 | 45 | 98 | 72 |
| 2 | 0.065 | 0.25 | 40 | 94 | 108 |
| 3 | 0.040 | 0.25 | 65 | 92 | 146 |

The foregoing description is intended as illustrative and are not to be taken as limiting. Still other variations are possible without departing from the spirit and scope of this invention and will readily present themselves to one skilled in the art.

What is claimed is:

1. A method of absorbing aqueous vaginal fluids comprising the steps of:

a) inserting a first absorbent device into a vaginal cavity, the absorbent device comprising an absorbent body and an indicator structure arranged and configured within the absorbent body, the indicator structure comprising a resilient member maintained in a strained configuration by a restraint; wherein the resilient member is capable of reverting to a relaxed configuration upon the weakening of the restraint and the restraint weakens upon exposure to moisture b) allowing the first absorbent device to absorb sufficient aqueous vaginal fluids to weaken the restraint and to permit the resilient member to revert to the relaxed configuration;

c) detecting changed dimensions of the first absorbent device caused by the reversion of the resilient member to the relaxed configuration, while inserted; and d) removing the first absorbent device from the vaginal cavity.

2. The method of claim 1 further comprising the step of inserting a second absorbent device into the vaginal cavity after the step of removing the first absorbent device from the vaginal cavity.

* * * * *